United States Patent
Petit et al.

(10) Patent No.: US 6,759,399 B1
(45) Date of Patent: Jul. 6, 2004

(54) USE OF ANTIMINERALOCORTICOID COMPOUNDS AGAINST NARCOTIC WITHDRAWAL SYNDROME

(75) Inventors: Francis Petit, Colombes (FR); Daniel Philibert, La-Varenne-Saint-Hilaire (FR); Nick Goeders, Shreveport, LA (US)

(73) Assignee: Aventis Pharma S.A. (FR)

( * ) Notice: Subject to any disclaimer, the term of this patent is extended or adjusted under 35 U.S.C. 154(b) by 0 days.

(21) Appl. No.: 09/535,711

(22) Filed: Mar. 27, 2000

Related U.S. Application Data

(62) Division of application No. 09/043,382, filed as application No. PCT/FR96/01459 on Sep. 19, 1996.

(30) Foreign Application Priority Data

Sep. 21, 1995 (FR) ............................................ 95 11086

(51) Int. Cl.$^7$ .......................... A61K 31/56; A61K 31/59
(52) U.S. Cl. .................. 514/175; 514/169; 514/170; 514/172; 514/173; 514/175; 514/176; 514/179; 514/180; 514/182
(58) Field of Search ................................ 514/170, 172, 514/173, 175, 176, 179, 180, 182, 178

(56) References Cited

U.S. PATENT DOCUMENTS 5,413,993 A * 5/1995 Soma et al. .................. 514/54

OTHER PUBLICATIONS

Eur. J. Pharmcol., vol. 56, No. 3, 1979 pp. 197–205.*

J. Pharmacol. Exp. Ther, vol. 236, No. 1, 1986, pp. 157–165.*

Fed. Proc. Vol 40, No. 5, 1981 pp. 1502–1507.*

Farmakol. Tokosikol, vol. 41, No. 5, 1978, pp. 541–533.*

Wei, E. (CA 79:49219, abstract of Brit. J. Pharmacol. (1973), 47(4), 693–9).*

El'tsova et al.(CA 89:191592, abstract of Farmkol. Tokshikol, (Moscow), 1978, 41(5), 541–4).*

Budziszwska et al. (CA 125:49548, abstract of Eur. Neuropsychopharmacol. (1996), 6(2), 135–140).*

Goodman and Gilman (The Pharmaceutical Basis of Therapeutics, 7$^{th}$ edition, Macmillan Publishing Company, New York, 1985 pp. 568–571).*

* cited by examiner

*Primary Examiner*—Sabiha Qazi
(74) *Attorney, Agent, or Firm*—Muserlian, Lucas and Mercanti

(57) ABSTRACT

The method of treating narcotic withdrawal symptoms in warm-blooded animals comprising administering to warm-blooded animals in need thereof an amount of a compound having anti-mineralocorticoid activity sufficient to treat narcotic withdrawal symptoms.

7 Claims, No Drawings

USE OF ANTIMINERALOCORTICOID COMPOUNDS AGAINST NARCOTIC WITHDRAWAL SYNDROME

PRIOR APPLICATIONS

This application is a divisional of U.S. patent application Ser. No. 09/043,382 filed Mar. 16, 1998 which is a 371 of PCT/FR96/01459 filed Sep. 19, 1996.

Use of compounds having an antimineralocorticoid activity for the preparation of medicaments intended for the prevention or treatment of symptoms linked to drug dependence or to the spontaneous or induced withdrawal syndrome, caused by narcotics and the compositions containing them.

The products having an antimineralocorticoid activity are known as being able to be used as medicaments. They are, in particular, antagonists of aldosterone and they increase salt and water diuresis with conservation of organic potassium; moreover they have, for some, the advantage of being devoid of hormonal side-effects, in particular anti-androgen and anti-estrogen effects. They can therefore be used to combat, in particular, arterial hypertension and cardiac insufficiencies.

There are two major types of glucocorticoid receptor at the level of the central nervous system, the type I receptor and the type II receptor (R. Ahima et al. J. Comp. Neurol. 313 (1991) 522–528; Neuroscience 39 (1990) 579–604).

The type I receptor, at the level of the brain, is identical to the standard mineralocorticoid receptor found at the level of the kidney, and it has a high affinity and a low bonding capacity for the endogenous glucocorticoids. In others terms, an antimineralocorticoid behaves at the level the central nervous system as a type I antiglucocorticoid.

The Applicant has demonstrated the new and unexpected use of these products, mentioned above.

It has previously been shown that the glucocorticoids (dexamethasone type) antagonize the analgesic activity of morphine while an antagonist of the glucocorticoids, of 17β-hydroxy 11β-(4-dimethylaminophenyl) 17α-(prop-1-ynyl) estra 4,9-diene-3-one type, or a suprarenalectomy, potentializes this activity (Capasso et al. Life Science 51 139 (1992), Ratka et al. Neuroendocrinology 49 439 (1988) Pieretti et al. Gen. Pharmacol. 22 929 (1991)).

However, to the knowledge of the Applicant, nobody has demonstrated the activity of an antimineralocorticoid vis-à-vis the undesirable effects of opiates and in particular of the induction of a physical or psychological dependent state and the withdrawal syndrome associated with this state. These dependence and withdrawal phenomena involve complex central mechanisms, multiple and different from those which are observed in the analgesic activity of opiates.

On the other hand, recent data has been reported on the important role that the endogenous glucocorticoids could play in the symptoms of narcotic withdrawal, as well as in the dependence phenomena induced by opiates or cocaine. Thus, hypercortisolism has been observed in man over the course of clinical trials, during withdrawal spontaneous or induced by naloxone consecutive with taking heroin or morphine (Cami et al. Br. J. Addict 87 1145 (1992), Higgins et al. Drug Alcohol Depend. 30 13 (1992). Other elements reported in animals show an activation of the hypothalamo-surrenal axis by cocaine (Borowsky and Kuhn, J. Pharmacol. Exp. Ther. (1991) 256, 204) administered in an acute or repeated treatment with an increase in plasmatic levels of corticosterone and ACTH (Moldow and Fischman, Peptides 8 819 (1987), Yang et al. Pharmacol. Biochem Behau. 41 643 (1992); Saphier et al. Neuroendocrinology 57 54 (1993)) consecutive with a mediation of monoaminergic origin (dopamine for example). For example the involvement of the dopaminergic system appears confirmed by the fact that haloperidol and metoclopramide (dopaminergic antagonists) oppose respectively the increase in corticosterone levels induced by cocaine and the phenomenon of morphinic withdrawal (Ramaswamy and Bapna, Life Science 40 807 (1987)).

This data appears to show that the endogenous glucocorticoids could intervene in the phenomena of withdrawal and dependence, in the same way as dopaminergic mechanisms but at a stage further upstream than the latter.

These different elements have justified the study of antagonists of mineralocorticoids in particular vis-à-vis the phenomena of physical and psychological dependence or morphinic withdrawal syndrome induced by naloxone in animals since no data is currently available on the activity of this therapeutic class in this axis.

In fact, while an increase in endogenous glucocorticoid levels has been reported in opiate withdrawal phenomena, it has not been demonstrated that this increase could have a physiopathological repercussion and that in particular the blocking of these endogenous glucocorticoids at the level of their receptors by an antimineralocorticoid would be translated into a beneficial effect on physical and psychological dependence and on the symptoms of the withdrawal syndrome.

Thus, the Applicant has demonstrated a new and unexpected use of antimineralocorticoids.

Therefore a subject of the present invention is the use of compounds having an antimineralocorticoid activity for the preparation of medicaments intended for the prevention or treatment of symptoms linked to drug dependence or to the spontaneous or induced withdrawal syndrome, caused by narcotics or mixtures of narcotics.

By compounds having an antimineralocorticoid activity is meant, either compounds which are antagonists of the aldosterone receptor, which compounds are competitive inhibitors of the steroid bond to its receptor, thus preventing the natural hormone from carrying out its activity, or compounds which inhibit the biosynthesis of aldosterone, by inhibiting in particular 18-hydroxylase. In fact, the oxidation in position 18 constitutes the last stage of the biosynthesis of aldosterone and a selective inhibition of this stage allows, in principle, the inhibition of biosynthesis of other essential steroid hormones such as cortisol or androstanedione to be avoided. These compounds are essentially represented by the compounds of Figure $(I_j)$ described below in which $R_{4j}$ is an alkenyl or alkynyl group and $R_{5j}$ is either a hydroxyl radical, or a hydrogen atom.

By narcotics is meant all drugs entailing a psychological and physical dependence phenomenon and the spontaneous or induced stopping of which leads to a withdrawal syndrome. There can be mentioned:

1) natural morphinomimetics such as:
   a) the opium alkaloids, for example morphine,
   b) the alkaloid derivatives of morphine, for example heroin or codeine, 2) synthetic morphinomimetics such as:
a) piperidine derivatives, for example pethidine or
b) methadone and its derivatives, for example dextromoramide,
3) cocaine,
as well as all combinations containing two or more of these narcotic products.

A more particular subject of the present invention is the use of compounds having an antimineralocorticoid activity for the preparation of medicaments intended for the prevention or treatment of symptoms linked to dependence or spontaneous or precipitated withdrawal syndrome caused by morphinomimetic narcotics chosen from heroin, morphine and methadone.

A more particular subject of the present invention is the use of compounds having an antimineralocorticoid activity for the preparation of medicaments intended for the prevention or treatment of symptoms linked to dependence or spontaneous or precipitated withdrawal syndrome caused by cocaine.

A more particular subject of the present invention is the use as defined previously, characterized in that compounds having an antimineralocorticoid activity correspond to general formula (I):

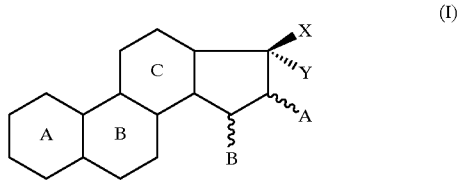

in which rings A, B and C have one of the following structures:

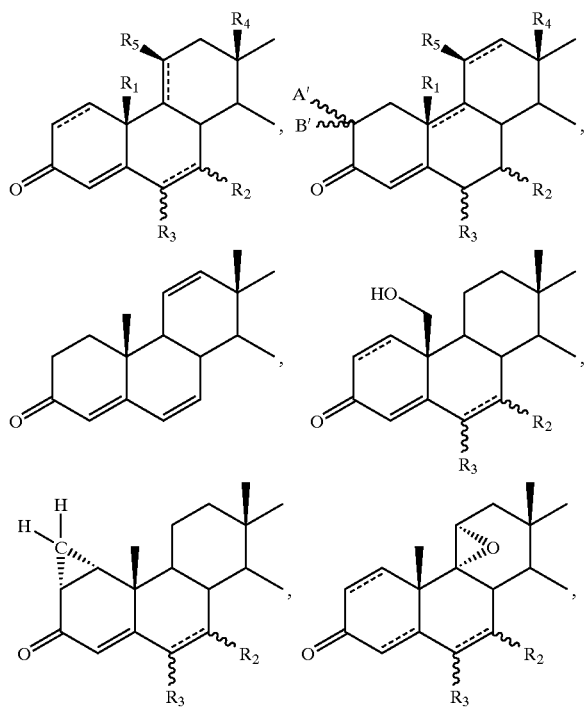

and in which:
either X and Y represent the groups:

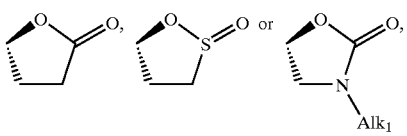

$Alk_1$ representing an alkyl group containing at most 8 carbon atoms, or X represents a hydroxyl, acetyloxy, propionyloxy, methoxy or ethoxy radical and Y represents a $CH_2CH_2CO_2M$, $CH_2CH_2SO_2M$ or $CH_2CH_2CH_2OH$ radical, M being a hydrogen atom, an alkali metal atom or an ammonium radical, or X represents a $COCH_2Z$ radical, in which Z represents a hydrogen atom, a hydroxyl radical or an acyloxy radical containing 1 to 18 carbon atoms, and Y represents a hydrogen atom, or X represents a

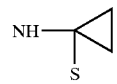

radical, S being an alkyl radical containing at most 8 carbon atoms, or a hydrogen atom and Y represents a hydrogen atom, A and B are hydrogen atoms or together form a methylenic bridge in position 15α, 16α or 15β, 16β, A' and B' are hydrogen atoms, alkyl radicals containing 1 to 4 carbon atoms, or form with the carbon which carries them a cyclopropyl radical, $R_1$ represents a methyl radical or a C≡C—W group, in which W represents either a hydrogen atom, or an alkyl radical containing at most 8 carbon atoms optionally substituted by a hydroxyl, free, esterified or salified carboxy, amino, tritylamino, chloroacetylamino, trifluoroacetylamino, halogen, monoalkylamino, dialkylamino radical, each alkyl radical containing at most 8 carbon atoms, or an aryl or aralkyl radical containing at most 14 carbon atoms, optionally substituted by a hydroxyl, free esterified or salified carboxy, amino, monoalkylamino, dialkylamino, alkyl, alkoxy or alkylthio radical, each alkyl radical containing at most 8 carbon atoms, or a halogen atom, or a trialkylsilyl radical, each alkyl radical containing at most 8 carbon atoms, $R_2$ and $R_3$ are such that
either $R_2$ and $R_3$ form together a methylenic bridge in position 6α, 7α or 6β, 7β, or $R_2$ and $R_3$ are hydrogen atoms, or $R_3$ is a hydrogen atom and $R_2$ represents a SCOCH3, CO2Alk group, Alk being an alkyl radical containing at most 8 carbon atoms, alkyl, alkenyl or alkynyl radicals containing at most 8 carbon atoms and optionally substituted by a hydroxyl, free, esterified or salified carboxy, halogen, amino, monoalkylamino, dialkylamino radical, each alkyl radical containing at most 8 carbon atoms, $R_4$ represents an alkyl, alkenyl or alkynyl radical containing at most 8 carbon atoms, $R_5$ represents either an allenyl radical, or a hydroxyl radical, or a hydrogen atom, the dotted lines represent a possible second bond, the wavy lines indicate that the substituents are in position α or β, as well as the salts of the products of formula (I) with pharmaceutically acceptable acids and bases.

By alkyl group containing at most 8 carbon atoms, is meant linear or branched alkyl radicals such as methyl, ethyl, n-propyl, iso-propyl, butyl, isobutyl, sec-butyl, tert-butyl, pentyl, isopentyl, sec-pentyl, tert-pentyl, neopentyl, hexyl, isohexyl, sec-hexyl, tert-hexyl, heptyl or octyl.

Alkyl radicals having at most 4 carbon atoms are preferred and in particular methyl, ethyl, propyl and isopropyl radicals.

When $R_4$ is an alkyl group, it is quite particularly the methyl radical.

The alkali metal atom which can be represented by M is preferably sodium, potassium or lithium.

By acyloxy radical is meant in particular formyloxy, acetoxy, propionyloxy, butyryloxy or benzoyloxy radicals.

As preferred values of W, there can be mentioned the hydrogen atom and alkyl radicals containing 1 to 8 carbon atoms optionally substituted by the radicals as described previously, and quite particularly the methyl radical.

As the preferred value of $R_1$, there can be mentioned the C≡C—H and C≡C—Me group.

The term optionally esterified carboxy designates alkyloxycarbonyl radicals containing at most 9 carbon atoms, such as for example methoxycarbonyl, ethoxycarbonyl, propoxycarbonyl, n-butyloxycarbonyl, tert-butyloxycarbonyl or also benzyloxycarbonyl radicals.

The terms monoalkylamino and dialkylamino designate the amino radical substituted by one or two alkyl radicals as defined above. In particular it is the methylamino and dimethylamino radicals.

By halogen atom, is meant quite particularly chlorine and bromine atoms.

The aryl and aralkyl radicals which can be represented by W are preferably a phenyl, benzyl or phenethyl radical.

The term alkoxy designates alkoxy radicals containing 1 to 8 carbon atoms such as for example methoxy or ethoxy.

The term alkylthio designates alkylthio radicals containing 1 to 8 carbon atoms such as for example methylthio or ethylthio.

The term alkenyl designates a linear or branched alkenyl radical such as for example vinyl, allyl, 1-propenyl, butenyl, pentenyl or hexenyl radicals.

Among the alkenyl radicals, there are preferred those with 4 carbon atoms such as allyl, propenyl or butenyl radicals.

The term alkynyl designates a linear or branched alkynyl radical, having at most 12 carbon atoms such as ethynyl, propargyl, butynyl, pentynyl or hexynyl radicals.

Among the alkynyl radicals, there are preferred those with 4 carbon atoms such as the propargyl radical.

When $R_4$ is an alkenyl or alkynyl group, it is quite particularly a $CH_2$—C≡CH or $CH_2$—CH=$CH_2$ radical.

When $R_3$ is a hydrogen atom and when the dotted line does not represent a double bond, $R_2$ is preferably found in position α.

When the products of formula (I) contain a carboxy function, this can be salified. Among the possible salts, there can be mentioned for example the salts of sodium, potassium, lithium, calcium, magnesium or ammonium. There can be mentioned, for the organic bases, methylamine, propylamine, trimethylamine, diethylamine, triethylamine, N,N-dimethylethanolamine, tri-(hydroxymethyl) amino methane, ethanolamine, pyridine, picoline, dicyclohexylamine, morpholine, benzylamine, procaine, lysine, arginine, histidine, N-methylglucamine.

When the products of formula (I) contain a function which can be salified with an acid and in particular an amino function, addition salts are obtained with acids.

The invention naturally extends to the addition salts with acids of the compounds of formula (I), which can be salified, such as for example salts formed with the following acids:

hydrochloric, hydrobromic, nitric, sulphuric, phosphoric, acetic, formic, propionic, benzoic, maleic, fumaric, succinic, tartaric, citric, oxalic, glyoxylic, aspartic, alkane sulphonics such as methane or ethane sulphonics, arylsulphonics, such as benzene or paratoluene sulphonics and arylcarboxylics.

The products of formula (I) are known or are prepared according to methods known to a person skilled in the art.

A more precise subject of the present invention is the use as defined previously, characterized in that the compounds having an antimineralocorticoid activity corresponding to general formula ($I_a$):

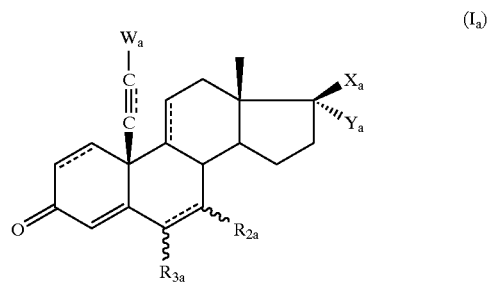

in which:

either $X_a$ and $Y_a$ represent the groups

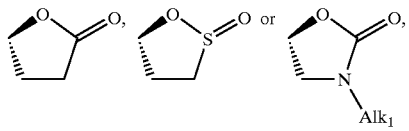

$Alk_1$ being as defined previously, or Xa represents a hydroxyl, acetyloxy, propionyloxy, methoxy or ethoxy radical and $Y_a$ represents a $CH_2CH_2CO_2M$, $CH_2CH_2SO_2M$ or $CH_2CH_2CH_2OH$ radical, M being as defined previously, $R_{2a}$, $R_{3a}$ and $W_a$ respectively have the same values as $R_2$, $R_3$ and W as defined previously and the dotted or wavy lines retain the same meaning as previously.

A quite particular subject of the present invention is the use as defined previously of the products corresponding to general formula ($I_a$) chosen from the following list:

γ-lactone of 10β-ethynyl 17β-hydroxy 3-oxo-19-nor-17α-pregna-4,9 (11)-diene-21-carboxylic acid, γ-lactone of 17β-hydroxy 3-oxo-10β-(1-propynyl)-19-nor-17α-pregna-4,9 (11)-diene-21-carboxylic acid, γ-lactone of 17β-hydroxy 3-oxo-10β-(1-propynyl)-19-nor-17α-pregn-4-ene-21-carboxylic acid, γ-lactone of 10β-ethynyl 17β-hydroxy 3-oxo-19-nor-17α-pregn-4-ene-21-carboxylic acid.

The products of general formula ($I_a$) are described and prepared in the Patent Applications EP 0176399-A1 and EP 0237397-A1 and by methods known to a person skilled in the art.

A more precise subject of the present invention is the use as defined previously, characterized in that the compounds having an antimineralocorticoid activity correspond to general formula ($I_b$):

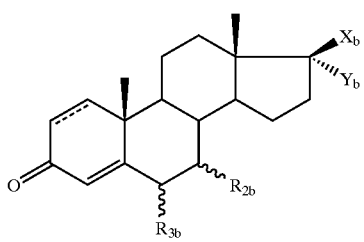 (I_b)

in which:

either $X_b$ and $Y_b$ represent the groups

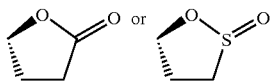

or $X_b$ represents a hydroxyl radical and $Y_b$ represents a $CH_2CH_2CO_2M$ radical, M being as defined previously, $R_{2b}$ and $R_{3b}$ are such that either $R_{2b}$ represents an alkyl, alkenyl or alkynyl radical optionally substituted as defined previously and $R_{3b}$ is a hydrogen atom, or $R_{2b}$ and $R_{3b}$ together form a methylenic bridge in position 6α,7α or in position 6β,7β.

When $R_{2b}$ is an alkyl group, it will be quite particularly the propyl radical in position α.

A quite particular subject of the present invention is the use as defined previously, of the products corresponding to general formula ($I_b$) chosen from the following list:

- (17R)-6β,7β-methylene-2'-oxydospiro-(androst-4-ene-17,5'-(1',2')-oxathiolane)-3-one
- (17R)-6α,7α-methylene-2'-oxydospiro-(androst-4-ene-17,5'-(1',2')-oxathiolane)-3-one
- (17R)-7α-methyl-2'-oxydospiro-(androst-4-ene-17,5'-(1',2')-oxathiolane)-3-one
- (17R)-7α-n-propyl-2'-oxydospiro-(androst-4-ene-17,5'-(1',2')-oxathiolane)-3-one
- γ-lactone of 17β-hydroxy-3-oxo-7α-propyl-17α-pregna-1,4-diene-21-carboxylic acid,
- potassium 17β-hydroxy-3-oxo-7α-propyl-17α-pregna-1,4-diene-21-carboxylate,
- γ-lactone of 17β-hydroxy-3-oxo-7α-propyl-(17α)-pregn-4-ene-21-carboxylic acid,
- potassium 17β-hydroxy-3-oxo-7α-propyl-(17α)-pregn-4-ene-21-carboxylate The products of formula (Ib) are prepared in the Patent Applications EP 0018245A, EP 0055170A, FR 2344286, FR 2421913, FR 2465749, and by methods known to a person skilled in the art.

A more precise subject of the present invention is the use as defined previously, characterized in that the compounds having an antimineralocorticoid activity, corresponding to general formula ($I_c$):

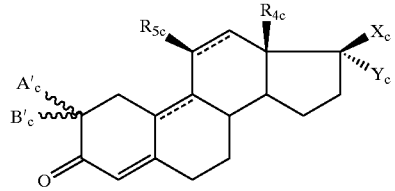 (I_c)

in which
either $X_c$ and $Y_c$ represent a group

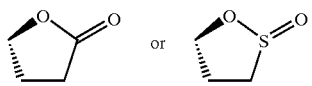

or $X_c$ represents a hydroxyl radical and $Y_c$ represents a $CH_2CH_2CO_2M$ or $CH_2CH_2SO_2M$ group, M being as defined previously, or $X_c$ represents a $COCH_2Z$ radical in which Z is as defined previously and $Y_c$ is a hydrogen atom, $A'_c$ and $B'_c$ respectively have the same values as A' and B' as defined previously, $R_{4c}$ is a methyl or ethyl radical, $R_{5c}$ is either a hydrogen atom, or an allenyl radical, it being understood that when $R_{5c}$ is an allenyl radical, $A'_c$ and $B'_c$ are hydrogen atoms, $R_{4c}$ is a methyl radical, $X_c$ and $Y_c$ together form a

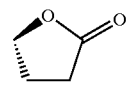

group,
the dotted lines in position 9–10 form a second bond, and those in position 11–12 do not form a second bond.

A quite particular subject of the present invention is the use as defined previously of the products corresponding to general formula ($I_c$) chosen from the following list:

- 2,2-dimethyl 19-nor pregn-4-ene-3,20-dione,
- 21-acetoxy 2,2-dimethyl 19-nor-pregn-4-ene 3,20-dione,
- 2,2-dimethyl 21-hydroxy 19-nor-pregn-4-ene 3,20-dione,
- 2,2-dimethyl 19-nor-pregna-4,9-diene 3,20-dione,
- 21-acetoxy 2,2-dimethyl 19-nor-pregna-4,9-dien 3,20-dione,
- 2,2-dimethyl 21-hydroxy 19-nor-pregna-4,9-dien 3,20-dione,
- 2,2-dimethyl 19-nor-pregna-4,9,11-triene 3,20-dione,
- 21-acetoxy 2,2-dimethyl 19-nor-pregna-4,9,11-triene 3,20-dione,
- 2,2-dimethyl 21-hydroxy 19-nor-pregna-4,9,11-triene 3,20-dione,
- (17R) 2'-oxydospiro-(estra-4,9-diene-17,5'-(1',2')-oxathiolane) 3-one,
- (17R) 2'-oxydospiro-(estra-4,9,11-triene-17,5'-(1',2')-oxathiolane) 3-one,
- (17R) 11β-hydroxy 2'-oxydospiro-(estra-4,9-diene-17,5'-(1',2')-oxathiolane) 3-one,
- 2,2-dimethyl-13-ethyl-21-hydroxy-18,19-dinor-pregn-4-ene 3,20-dione,
- γ-lactone of 11β-allenyl-17β-hydroxy-3-oxo-19-nor-17-pregna-4,9-diene-21-carboxylic acid.

The products of general formula ($I_c$) are described and prepared in Patent Applications FR 2364655, FR 2374037, EP 0012641, in the following publication: G. AUZOU et al. J. Med. Chem. (1993) 36 2404–2407, and by methods known to a person skilled in the art.

A more precise subject of the present invention is the use as defined previously characterized in that the compounds having an antimineralocorticoid activity corresponding to general formula ($I_d$):

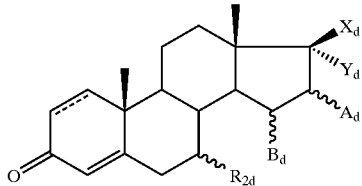

in which:
either $X_d$ and $Y_d$ represent the group

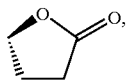

or $X_d$ represents a hydroxyl radical and $Y_d$ represents a $CH_2CH_2CO_2M$ radical, M being as defined previously,
$A_d$ and $B_d$ respectively have the same values as A and B as defined previously,
$R_{2d}$ represents either a thioacetyl radical, or a $CO_2Alk$ radical, Alk being an alkyl radical containing at most 8 carbon atoms. It is preferably a methyl, ethyl and isopropyl radical, and the dotted or wavy lines keep the same meaning as previously.

A quite particular subject of the present invention is the use as defined previously of the products corresponding to general formula ($I_d$) chosen from the following list:
  γ-lactone of 7α-acetylthio-17β-hydroxy-15β,16β-methylene-3-oxo-17α-pregna-1,4-diene-21-carboxylic acid (Mespirenone),
  γ-lactone of 17β-hydroxy-7α-methoxycarbonyl-15β,16β-methylene-3-oxo-17α-pregn-4-ene-21-carboxylic acid (ZK91587),
  γ-lactone of 7α-acetylthio-17β-hydroxy-3-oxo-17α-pregn-4-ene-21-carboxylic acid (Spironolactone),
  γ-lactone of 17β-hydroxy-7α-methoxycarbonyl-3-oxo-17α-pregn-4-ene-21-carboxylic acid (Mexrenone),
  the potassium salt of 17β-hydroxy-7α-methoxycarbonyl-3-oxo-pregn-4-ene-21-carboxylic acid.

The products of formula ($I_d$) are commercial products or are prepared or described in the following Patent Applications or publications:
  Mespirenone: Drug of the Future Vol. 12 No. 1 (1987) 27,
  Mexrenone: G. B. Cutler et al. J. Pharmacol. and Exp. Ther. (1979) 209 144,
  ZK 91587: H. J. Grill et al. J. Ster. Biochem, 23 (Suppl.) Abst. 19 (1985),
  Spironolactone: J. A. Cella and C. M. Kawaga J. Am. Chem. Soc. (1957) 79 4808,
  K. Mexrenoate: L. M. Hoffmann et al. The Journal of Pharmacol. and Exp. Ther. (1977) 102 (3) 762, or according to methods known to a person skilled in the art.

A more precise subject of the present invention is the use as defined previously, characterized in that the compounds having an antimineralocorticoid activity correspond general ormula ($I_e$):

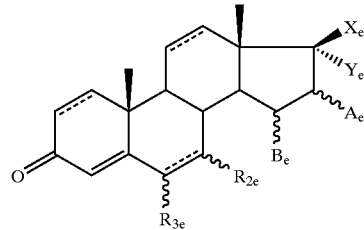

in which:
either $X_e$ and $Y_e$ represent the group

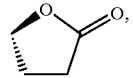

or $X_e$ represents a hydroxyl radical and $Y_e$ represents a $CH_2CH_2CO_2M$ radical, M being as defined previously,
$R_{2e}$ or $R_{3e}$ are such that:
either $R_{2e}$ and $R_{3e}$ together form a methylenic bridge in position 6α,7α or 6β,7β,
or $R_{2e}$ and $R_{3e}$ are hydrogen atoms,
$A_e$ and $B_e$ respectively have the same values as A and B as defined previously, the dotted or wavy lines keeping their previous meaning. A quite particular subject of the present invention is the use as defined previously of the products corresponding to general formula ($I_e$), chosen from the following list:
  γ-lactone of 17β-hydroxy-6β,7β,15β,16β-dimethylene-3-oxo-17α-pregna-1,4-diene-21-carboxylic acid (Spirorenone),
  γ-lactone of 17β-hydroxy-6β,7β,15β,16β-dimethylene-3-oxo-17α-pregna-4-ene-21-carboxylic acid (dihydrospirorenone),
  γ-lactone of 17β-hydroxy-3-oxo-17α-pregna-4,6,11-triene-21-carboxylic acid,
  γ-lactone of 17β-hydroxy-3-oxo-17α-pregna-4,6-diene-21-carboxylic acid (Canrenone),
  the potassium salt of 17β-hydroxy-3-oxo-17α-pregna-4,6-diene-21-carboxylic acid (potassium Canrenoate),
  γ-lactone of 17β-hydroxy-6β,7β-methylene-3-oxo-17α-pregn-4-ene-21-carboxylic acid (Prorenone),
  potassium salt of 17β-hydroxy-6β,7β-methylene-3-oxo-17α-pregn-4-en-21-carboxylic acid (potassium protenoate).

The products of formula ($I_e$) are commercial products or are prepared or described in the following Patent Applications or publications:
  Spirorenone: W. Losert et al Arzneim-Forsch/Drug. Res. (1986) 36 1583,
  Dihydrospirorenone: DE 2652761-A,
  K canrenoate: L. E. Ramsay et al. Adrenal Steroid Antagonism. Ed. M. K. Agarwal Berlin, N.Y. 1984,
  Prorenone, K prorenoate: J. Casals-Stenzel et al. Arch. Pharmacol. Suppl. 316 (1981) R49,
  γ-lactone of 17β-hydroxy-3-oxo-17α-pregna-4,6,11-triene-21-carboxylic acid, Anu. Drug. Data Rep. (1985) 7 (2) 94.

A quite particular subject of the present invention is the use as defined previously, characterized in that the compounds having an antimineralocorticoid activity correspond to general formula ($I_f$):

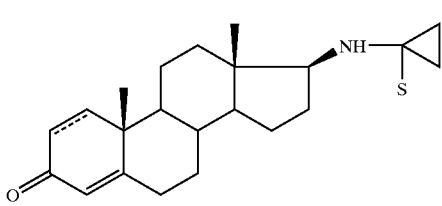

(I_f)

in which S represents an alkyl radical containing 1 to 8 carbon atoms, or a hydrogen atom.

The products of general formula (I_f) are described in Patent Application EP 402857-A.

A more particular subject of the present invention is the use as defined previously, characterized in that the compounds having an antimineralocorticoid activity correspond to general formula (I_g):

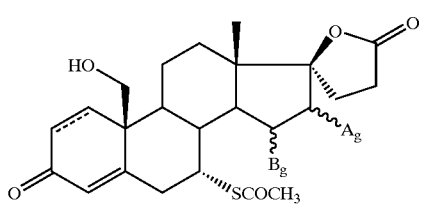

(I_g)

in which $A_g$ and $B_g$ respectively have the same values as A and B as defined previously, the dotted or wavy lines keeping the same meaning as previously.

The products of general formula (I_g) are described in Anu. Drug. Data Rep. (1986) 8 (9) 824.

A more particular subject of the present invention is the use as defined previously, characterized in that the compounds having an antimineralocorticoid activity corresponding to general formula (I_h):

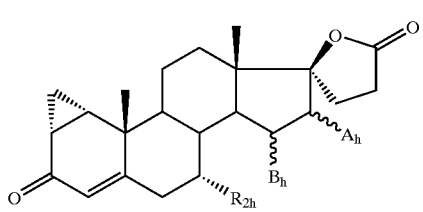

(I_h)

in which $A_h$, $B_h$ and $R_{2h}$ respectively have the same values as A, B and $R_2$ as defined previously.

The products of general formula (I_h) are described in Anu. Drug. Data Rep. (1985) 7(5) 295, (1986) 8(2) 152.

A more particular subject of the present invention is the use as defined previously, characterized in that the compounds having an antimineralocorticoid activity correspond general formula (I_i):

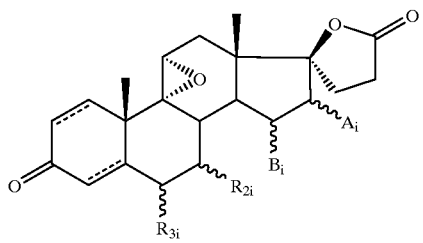

(I_i)

in which $A_i$, $B_i$, $R_{2i}$ and $R_{3i}$ respectively have the same values as A, B, $R_2$ and $R_3$ as defined previously.

The products of general formula products (I_i) are described in Anu. Drug. Data Rep. (1985) 7(5) 295, (1986) 8(9) 824.

A more precise subject of the present invention is the use as defined previously, characterized in that the compounds having an antimineralocorticoid activity correspond to general formula (I_j):

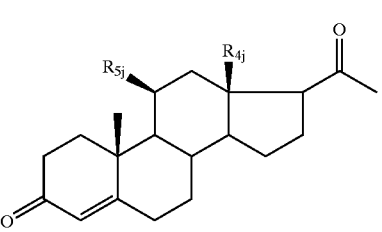

(I_j)

in which $R_{4j}$ is an alkenyl or alkynyl group containing 1 to 8 carbon atoms and $R_{5j}$ is a hydroxyl radical or a hydrogen atom.

A quite particular subject of the present invention is the use as defined previously, of the products corresponding to general formula (I_j) in which
either $R_{4j}$ is a —CH$_2$—CH=CH$_2$, CH=CH$_2$, CH$_2$—C≡CH radical and $R_{5j}$ is a hydrogen,
or $R_{4j}$ is a —CH$_2$—C≡CH radical and $R_{5j}$ is an OH radical.

The products of formula (I_j) are inhibitors of the biosynthesis of aldosterone. They are described in the following publications:

A. Viger et al., Tetrahedron (1988) 44 1127, J. Steroid Biochem. (1988) 30 469,

B. W. Metcalf et al., Tet. Lett. (1985) 26 1137–1140.

The invention extends to the pharmaceutical compositions containing at least one medicament as defined above as active ingredient, intended for the prevention or treatment of symptoms linked to drug dependence or to the spontaneous or induced withdrawal syndrome, caused by narcotics or mixtures of narcotics.

The compounds of the invention are used by digestive, parenteral or local route, for example by percutaneous route. They can be prescribed in the form of plain or sugar-coated tablets, capsules, granules, suppositories, pessaries, injectable preparations, ointments, creams, gels, microspheres, implants, patches, which are prepared according to the usual methods.

The active ingredient or ingredients can be incorporated with excipients usually employed in these pharmaceutical compositions, such as talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents, preservatives.

In particular, the invention extends to the pharmaceutical compositions containing as active principle at least one medicament as defined above, corresponding to any one of general formulae (I), ($I_a$), ($I_b$), ($I_c$), ($I_d$), ($I_e$), ($I_f$), ($I_g$), ($I_h$), ($I_i$) or ($I_j$), as defined previously.

More particularly the invention extends to the pharmaceutical compositions containing as active principle at least one medicament as defined above, chosen from the following list:

γ-lactone of 10β-ethynyl-17β-hydroxy 3-oxo-19-nor-17α-pregna-4,9(11)-diene-21-carboxylic acid, potassium 17β-hydroxy-3-oxo-7α-propyl-17α-pregn-4-ene-21-carboxylate, γ-lactone of 11β-allenyl-17β-hydroxy-3-oxo-19-nor-17α-pregna-4,9(11)-diene-21-carboxylic acid, γ-lactone of 17β-hydroxy-7α-methoxycarbonyl-15β,16β-methylene-3-oxo-17α-pregn-4-ene-21-carboxylic acid, γ-lactone of 7α-acetylthio-17β-hydroxy-3-oxo-17α-pregn-4-ene-21-carboxylic acid, γ-lactone of 17β-hydroxy-7α-methoxycarbonyl-3-oxo-17α-pregn-4-ene-21-carboxylic acid, γ-lactone of 17β-hydroxy-3-oxo-17α-pregn-4,6-diene-21-carboxylic acid 13β-(propen-2-yl)-18-nor-pregn-4-ene-3,20-dione.

The useful dose varies as a function of the type of withdrawal or dependence to be prevented or treated and the administration route. It can vary from 1 to 1000 mg per day for an adult by oral route.

PHARMACOLOGICAL STUDY

A) Evaluation of the Withdrawal Syndrome Induced by Naloxone in Mice

1—Equipment and Method.

1.1 Animals.

The experiments were carried out with male Swiss mice (Charles River, France) of a body weight comprised between 20 and 25 g. During the tests, the animals had free access to food and drinking water. The number of animals per group is 10 to 13 mice.

1.2 Products.

The following antimineralocorticoids (AM):

AM1 Spironolactone,

AM2 potassium 17β-hydroxy 3-oxo 7α-propyl-(17α)-pregn-4-ene-21-carboxylate.

were suspended in 0.5% methyl cellulose and administered by oral route (p.o). The morphine was put into solution in physiological serum and administered by sub-cutaneous (s.c) route. Finally, the naloxone hydrochloride was solubilized in distilled water and injected by intra-peritoneal route. All the products were administered to the animal under a volume of 25 ml/kg.

1.3 Treatment Methods and Doses Administered.

1.3.1 Treatment with Morphine: Induction of Morphinic Dependent State.

The first day (D1), the animals received 5 sub-cutaneous injections with increasing doses of morphine spread through the morning and at the beginning of the afternoon, at one hour intervals. On the following 3 days (D2, D3, D4), these same animals were treated in the morning with two administrations of the maximum dose used on day 1.

| Morphine-Doses (mg/kg, s.c.) | | | | Cumulative dose (mg/kg) |
|---|---|---|---|---|
| D1 | D2 | D3 | D4 | |
| 8 | 100 | 100 | 100 | 799 |
| 16 | 100 | 100 | 100 | |
| 25 | | | | |
| 50 | | | | |
| 100 | | | | |

1.3.2 Repeated Treatment with the Studied Products.

The antimineralocorticoids AM1 and AM2 were administered by oral route in the form of a daily treatment 2 hours before administration of the morphine and this took place for 4 days.

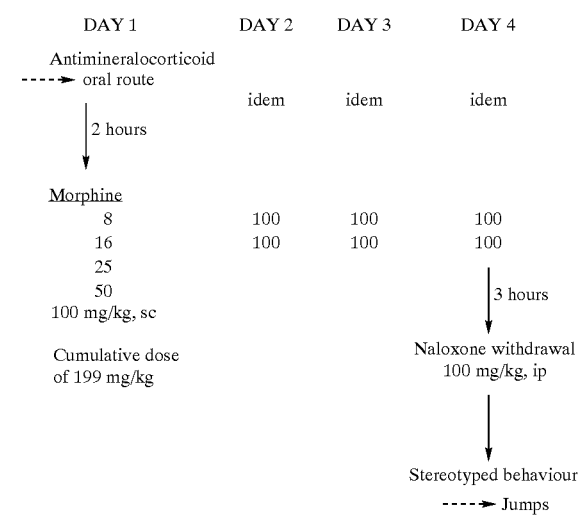

1.4 Operating Method

The technique used is inspired by that described by Way et al. J. Pharmacol. Exp. Ther. (1969), 167: 1–8 and Huidobro and Maggiolo Acta Physiol. Pharmacol. Latinoam. (1961), 11: 201–9. Thus, the repeated administration of a morphinic induces a phenomenon of physical dependence which can be easily demonstrated by the induction of a withdrawal syndrome using an opiate antagonist such as naloxone. This syndrome manifests itself, in mice in the form of stereotyped behaviour characterized by the appearance of repetitive jumps the number of which is related to the duration and intensity of the treatment by the morphinic.

The animals' withdrawal was carried out on the fourth day; three hours after the last treatment, using naloxone hydrochloride injected by intraperitoneal route at a dose of 100 mg/kg. Immediately after this injection, the animals were placed individually in Plexiglas cylinders (height=40 cm, diameter=20 cm). The number of consecutive jumps as a result of withdrawal and carried out by each animal was counted over a period of 10 minutes.

The results shown in tables represent the averages of thr individual values together with the standard error of the mean (m±sem).

2. Results.
2.1 Withdrawal Induced by Naloxone in Normal Mice Treated with Morphine.

|  | Doses (mg/kg) | Number of jumps/10 minutes (m ± sem) | % protection |
|---|---|---|---|
| Controls | 0 | 7 ± 5 |  |
| Morphine | 799 s.c. (cumulative over 4 days) | 76 ± 15 |  |
| AM1 | 4 × 10 p.o. | 3 ± 2 |  |
| Morphine + AM1 | 799 s.c. + 4 × 10 p.o. | 51 ± 7 | −33 |
| Controls | 0 | 0 |  |
| Morphine | 799 s.c. (cumulative over 4 days) | 114 ± 8 |  |
| AM1 | 4 × 20 p.o. | 11 ± 4 |  |
| Morphine + AM1 | 799 s.c. + 4 × 20 p.o. | 77 ± 8** | −32 | n = 10 mice/group; **p. < 0.01 according to the Dunnett test relative to the morphine group.

|  | Doses (mg/kg) | Number of jumps/10 minutes (m ± sem) | % protection |
|---|---|---|---|
| Controls | 0 | 0 |  |
| Morphine | 799 s.c. (cumulative over 4 days) | 99 ± 13 |  |
| AM2 | 4 × 20 p.o. | 4 ± 4 |  |
| Morphine + AM2 | 799 s.c. + 4 × 20 p.o. | 51 ± 8 | −48 |
| Controls | 0 | 7 ± 3 |  |
| Morphine | 799 s.c. (cumulative over 4 days) | 102 ± 10 |  |
| AM2 | 4 × 10 p.o. | 2 ± 2 |  |
| AM2 | 4 × 50 p.o. | 3 ± 2 |  |
| Morphine + AM2 | 799 s.c. + 4 × 10 p.o. | 76 ± 16 | −25 |
| Morphine + AM2 | 799 s.c. + 4 × 50 p.o. | 61 ± 8** | −40 | n = 10 mice/group; **p. < 0.01 according to the Dunnett test relative to the morphine group.

DISCUSSION-CONCLUSION

Co-administered for four days with morphine, the compound AM2 (4×20 mg/kg, p.o) significantly inhibits (−48%) the withdrawal syndrome induced by naloxone in mice dependent on morphine.

In conclusion, these results confirm the participation of endogenous glucocorticoids in the morphinic withdrawal syndrome, such as demonstrates itself in mice by stereotyped behaviour of jumping, since the latter is inhibited by antimineralocorticoids.

The antimineralocorticoid activity, through the results obtained with compounds AM1 and AM2 shows that an antagonist of the mineralocorticoids can have a beneficial effect in human clinical medicine in the prevention and treatment of narcotic withdrawal syndrome.

B) Evaluation of Dependence Induced by Cocaine
1—Method.

The anti-mineralocorticoid product AM2 was tested on 5 rats which were trained in the self-administration of cocaine during daily periods of one hour.

These rats were pre-treated 1 hour before the start of the self-administration sessions.

The product AM2 dissolved in a saline solution was administered by intra-peritoneal route. The doses range from 10 to 100 mg/kg.
2—Result.

The pre-treatment with 10 or 20 mg/kg of product AM2 has little or no effect on the self-administration of cocaine.

However, pre-treatment with 50 or 75 mg/kg of product AM2 leads to a significant reduction in the self-administration of cocaine.

3—Conclusion.

On the one hand these results suggest that the mineralocorticoid receptors are involved in the strengthening behaviour to cocaine.

On the other hand the antimineralocorticoid activity, through the results obtained with compound AM2 shows that an antagonist of the mineralocorticoids can have a beneficial effect in human clinical medicine in the treatment of dependence on narcotics and in particular cocaine.

What is claimed is:

1. A method of treating narcotic withdrawal symptoms in warm-blooded animals comprising administering to warm-blooded animals in need thereof an amount of a compound of the formula

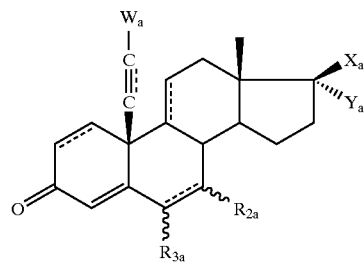

in which:
either $X_a$ and $Y_a$ are selected from the group consisting of

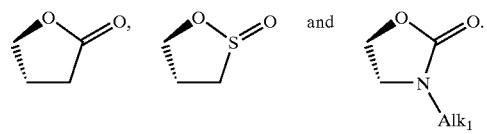

$Alk_1$ is alkyl of up to 8 carbon atoms,
or $X_a$ is selected from the group consisting of hydroxyl, acetyloxy, propionyloxy, methoxy and ethoxy and $Y_a$ is selected from the group consisting of —$CH_2CH_2CO_2M$, $CH_2CH_2SOM$ and $CH_2CH_2OH$, M is selected from the group consisting of hydrogen, $NR_1^+$ and alkali metal, $R_2$ and $R_3$ are such that either $R_2$ and $R_3$ form together a methylenic bridge in position 6α, 7α or 6β, 7β.
or $R_2$ and $R_3$ are hydrogen atoms,
or $R_3$ is a hydrogen atom and $R_2$ is a hydrogen atom and $R_2$ represents a $SCOCH_3$, $CO_2Alk$ group, Alk being an alkyl radical containing at most 8 carbon atoms, alkyl, alkenyl or alkynyl radicals containing at most 8 carbon atoms and optionally substituted by a hydroxyl, free esterified or salified carboxy, halogen, amino, monoalkylamino, dialkylamino radical, each alkyl radical containing at most 8 carbon atoms, W is eitehr hydrogen, or an alkyl radical containing at most 8 carbon atom, unsubstituted or substituted by a member selected from the group consisting of hydroxyl, free, esterified or salified carboxy, amino, tritylamino, chloroacetylamino, trifluoroacetylamino, halogen, monoalkylamino and dialkylamino, each alkyl having up to 8 carbon atoms, or an aryl or aralkyl of up to 14 carbon atoms, unsubstituted or substituted by a member selected from the group consisting of hydroxyl, free esterified or salified carboxy, amino, monoalkylamino, dialkylamino, alkyl, alkoxy and alkylthio, each alkyl having up to 8 carbon atoms, or halogen, or a trialkylsilyl, each alkyl having up to 8 carbon atoms, and the dotted line in a α-position second or wavy lines indicate an α- or β-position.

2. The method of claim 1 wherein the compound is selected from the group consisting of:

γ-lactone of 10β-ethynyl 17β-hydroxy 3-oxo-19-nor-17α-pregna-4,9(11)-diene-21-carboxylic acid, γ-lactone of 17β-hydroxy-3-oxo-10β-(1-propynyl)-19-nor-pregna-4,9(11)-diene-21 carboxylic acid, γ-lactone of 17β-hydroxy-3-10β-(1-propynyl)-19-nor-17α-pregn-4-ene-21-carboxylic acid, and -γ-lactone of 10β-ethynyl-17β-hydroxy-3-oxo-19-nor-17α-pregn-4-ene-21-carboxylic acid.

3. The method of claim 1 wherein the withdrawal symptoms are due to a morphinomimetic narcotic selected from the group consisting of heroin, morphine and methadone.

4. The method of claim 1 wherein the withdrawal symptoms are due to cocaine.

5. A composition for treating narcotic withdrawal symptoms comprising an amount of a compound of the formula

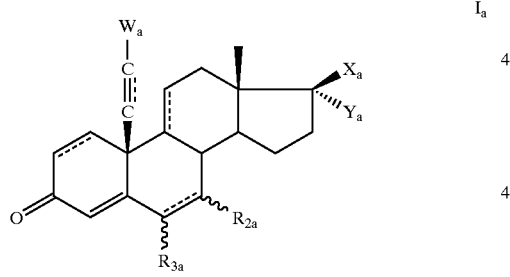

$I_a$ in which:

either $X_a$ and $Y_a$ are selected from the group consisting of

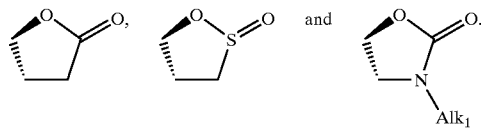

$Alk_1$ is alkyl of up to 8 carbon atoms, or $X_a$ is selected from the group consisting of hydroxyl, acetyloxy, propionyloxy, methoxy and ethoxy and $Y_a$ is selected from the group consisting of —$CH_2CH_2CO_2M$, $CH_2CH_2SOM$ and $CH_2CH_2OH$, M is selected from the group consisting of hydrogen, $NR_1^+$ and alkali metal, $R_2$ and $R_3$ are such that either $R_2$ and $R_3$ form together a methylenic bridge in position 6α, 7α or 6β, 7β, or $R_2$ and $R_3$ are hydrogen atoms, or $R_3$ is a hydrogen atom and $R_2$ is a hydrogen atom and $R_2$ represents a $SCOCH_3$, $CO_2Alk$ group, Alk being an alkyl radical containing at most 8 carbon atoms, alkyl, alkenyl or alkynyl radicals containing at most 8 carbon atoms and optionally substituted by a hydroxyl, free esterified or salified carboxy, halogen, amino, monoalkylamino, dialkylamino radical, each alkyl radical containing at most 8 carbon atoms, W is eitehr hydrogen, or an alkyl radical containing at most 8 carbon atoms unsubstituted or substituted by a member selected from the group consisting of hydroxyl, free, esterified or salified carboxy, amino, tritylamino, chloroacetylamino ,trifluoroacetylamino, halogen, monoalkylamino and dialkylamino, each alkyl having up to 8 carbon atoms, or an aryl or aralkyl of up to 14 carbon atoms, unsubstituted or substituted by a member selected from the group consisting of hydroxyl, free esterified or salified carboxy, amino, monoalkylamino, dialkylamino, alkyl, alkoxy and alkylthio, each alkyl having up to 8 carbon atoms, or halogen, or a trialkylsilyl, each alkyl having up to 8 carbon atoms, and the dotted line in a α-position second or wavy lines indicate an α- or β-position sufficient to treat said symptoms and an inert pharmaceutical carrier.

6. The composition of claim 5 wherein the withdrawal symptoms are due to a morphinomimetic narcotic selected from the group consisting of heroin, morphine and methadone.

7. The composition of claim 5 wherein the withdrawal symptoms are due to cocaine.

* * * * *